United States Patent [19]
Furuyoshi et al.

[11] Patent Number: 4,654,420
[45] Date of Patent: Mar. 31, 1987

[54] LIPOPROTEIN ADSORBENT FOR USE IN EXTRACORPOREAL CIRCULATION TREATMENT AND PROCESS FOR PREPARING THEREOF

[75] Inventors: Shigeo Furuyoshi, Kobe; Nobutaka Tani, Minoo, both of Japan

[73] Assignee: Kanegafuchi Kagaku Kogyo Kabushiki Kaisha, Osaka, Japan

[21] Appl. No.: 877,089

[22] Filed: Jun. 23, 1986

Related U.S. Application Data

[62] Division of Ser. No. 789,537, Oct. 21, 1985.

[30] Foreign Application Priority Data

Oct. 31, 1984 [JP] Japan ........ 59-231012
May 23, 1985 [JP] Japan ........ 60-110775

[51] Int. Cl.4 ........ C08G 18/10
[52] U.S. Cl. ........ 536/59; 521/53; 521/140; 521/149; 521/150; 530/359; 536/118
[58] Field of Search ........ 536/59, 118; 521/53; 106/122

[56] References Cited

U.S. PATENT DOCUMENTS 4,246,351 1/1981 Miyake et al. ........ 521/53
4,265,959 5/1981 Sano et al. ........ 521/53
4,266,030 5/1981 Tschong et al. ........ 521/53

*Primary Examiner*—Morton Foelak
*Attorney, Agent, or Firm*—Armstrong, Nikaido, Marmelstein & Kubovcik

[57] ABSTRACT

A lipoprotein adsorbent for use in extracorporeal circulation treatment which is made of a water-insoluble porous hard gel which has an exclusion limit value from $10^6$ to $10^9$ measured by using glubular proteins and comprises a polymer having hydroxy group in at least a part of the molecule, at least a part of hydroxy groups on the surface of said gel being converted to sulfates. By using the adsorbent of the present invention, LDL and VLDL can be selectively and effectively removed from the body fluids of the patient. Further, the adsorbent of the present invention can be prepared in a lower cost than the adsorbent based on the principle of the affinity chromatography, in which a relatively expensive ligand is employed.

4 Claims, 1 Drawing Figure

LIPOPROTEIN ADSORBENT FOR USE IN EXTRACORPOREAL CIRCULATION TREATMENT AND PROCESS FOR PREPARING THEREOF

This is a division, of application Ser. No. 789,537 filed Oct. 21, 1985.

BACKGROUND OF THE INVENTION

The present invention relates to a lipoprotein adsorbent for use in extracorporeal circulation treatment in order to remove harmful lipoproteins in blood, especially low density lipoproteins (hereinafter referred to as "LDL") and very low density lipoproteins (hereinafter referred to as "VLDL"), from blood, plasma or serum by selectively adsorbing the lipoproteins and a process for preparing thereof.

It has been known that LDL and VLDL among lipoproteins present in blood, contain a large amount of cholesterol and cause arteriosclerosis. In hypercholesterolemia such as familial hyperlipemia LDL shows several times higher values than those observed in normal conditions and causes coronary arteriosclerosis.

Although regimen or medication with probucol or cholestyramine have been employed for treatment of hypercholesterolemia such as familial hyperlipemia, they show only limited effect and have a fear of unfavorable side effects. Hitherto, familial hyperlipemia, in particular, can be effectively treated only by the so called plasma exchange therapy, where the plasma in the body of the patient is separated and exchanged with normal plasma or replacing fluid containing albumin. As is well known, however, the plasma exchange therapy has various defects, i.e.

(1) it needs to employ expensive fresh plasma or plasma fractions, (2) it removes not only harmful components but also effective ones, and (3) it has a danger to lead to infection by hepatitis viruses and the like.

A method for removing harmful components in blood by using a membrance has been adopted in order to overcome the above-mentioned defects. However, the method still has defects. For example, it does not have a sufficient selectivity and needs to supplement a part of proteins in plasma which are removed concurrently with the removal of harmful components.

Also, for the same purpose, a method using an immune adsorbent, in which an antibody is immobilized, has been employed. Though selectivity in the method is almost satisfactory, there exist many problems such as difficulty for obtaining the antibody, a high price of the antibody, difficulty for sterilizing adsorbent and poor stability of the adsorbent when preserving.

Furthermore, there has been adopted an adsorbent based on the principle of the affinity chromatography, wherein a compound having an affinity for harmful components (such compound is hereinafter referred to as "ligand") is immobilized. The adsorbent has a good selectivity and the ligand employed is not too expensive. However, it is required to lower the cost in order to use in extracorporeal circulation treatment in large quantities. Since the adsorbent based on the principle of the affinity chromatography has a carrier made of a soft gel such as agarose, it provides a poor flow rate of body fluids and frequently produces cloggings.

At a small cost, there has been known a lipoprotein adsorbent (by Maaskant, N. et al.) which is obtained by cross-linking polyvinyl sulfate (ester of polyvinyl alcohol and sulfuric acid) in an aqueous solution by applying $\gamma$ ray, which makes the resultant insoluble in water. However, in the method, where a porous gel which is made water-insoluble by cross-linking a water-soluble polymer previously converted to sulfate is obtained, the amount of the sulfuric acid residue decreases to a great extent as the cross-linking reaction proceeds and a solvent which can be employed in the cross-linking reaction is substantially restricted to water due to hydrophile property of the sulfuric acid residue in the polymer converted to sulfate, which results in a great restriction on the method of cross-linking which can be employed. Furthermore, there is a problem such as great difficulty in beads formation.

The adsorbent used in hemoperfusion or plasma perfusion therapy employing extracorporeal circulation (so-called plasmapheresis) is required to have enough mechanical strength (pressure durability) so that it can provide a large flow rate. The gel prepared as mentioned above, however, contains a polymer having an essentially high degree of hydrophile property and thus it cannot be a hard gel even though a water-insoluble gel is formed by the cross-linking and the like, which results in the gel being improper for use in extracorporeal circulation to cause consolidation.

The object of the present invention is to provide a safe and low-cost adsorbent for use in extracorporeal circulation treatment, which can selectively remove LDL and VLDL, by preparing a water-insoluble porous hard gel, followed by direct sulfation.

SUMMARY OF THE INVENTION

In accordance with the present invention, there can be provided a lipoprotein adsorbent for use in extracorporeal circulation treatment which is made of a water-insoluble porous hard gel which has an exclusion limit value from $10^6$ to $10^9$ measured by using globular proteins and comprises a polymer having hydroxy group in at least a part of the molecule, at least a part of hydroxy groups on the surface of said gel being sulfated. In accordance with the present invention, there can also be provided a process for preparing a lipoprotein adsorbent for use in extracorporeal circulation treatment, which is hard and has a great adsorbing capacity as well as an excellent selectivity, by forming a water-insoluble porous hard gel which has an exclusion limit value from $10^6$ to $10^9$ measured by using globular proteins and comprises a polymer having hydroxy group in at least a part of the molecule followed by direct conversion of hydroxy groups on the surface of said gel to sulfates.

DETAILED DESCRIPTION OF THE INVENTION

Figure 1:
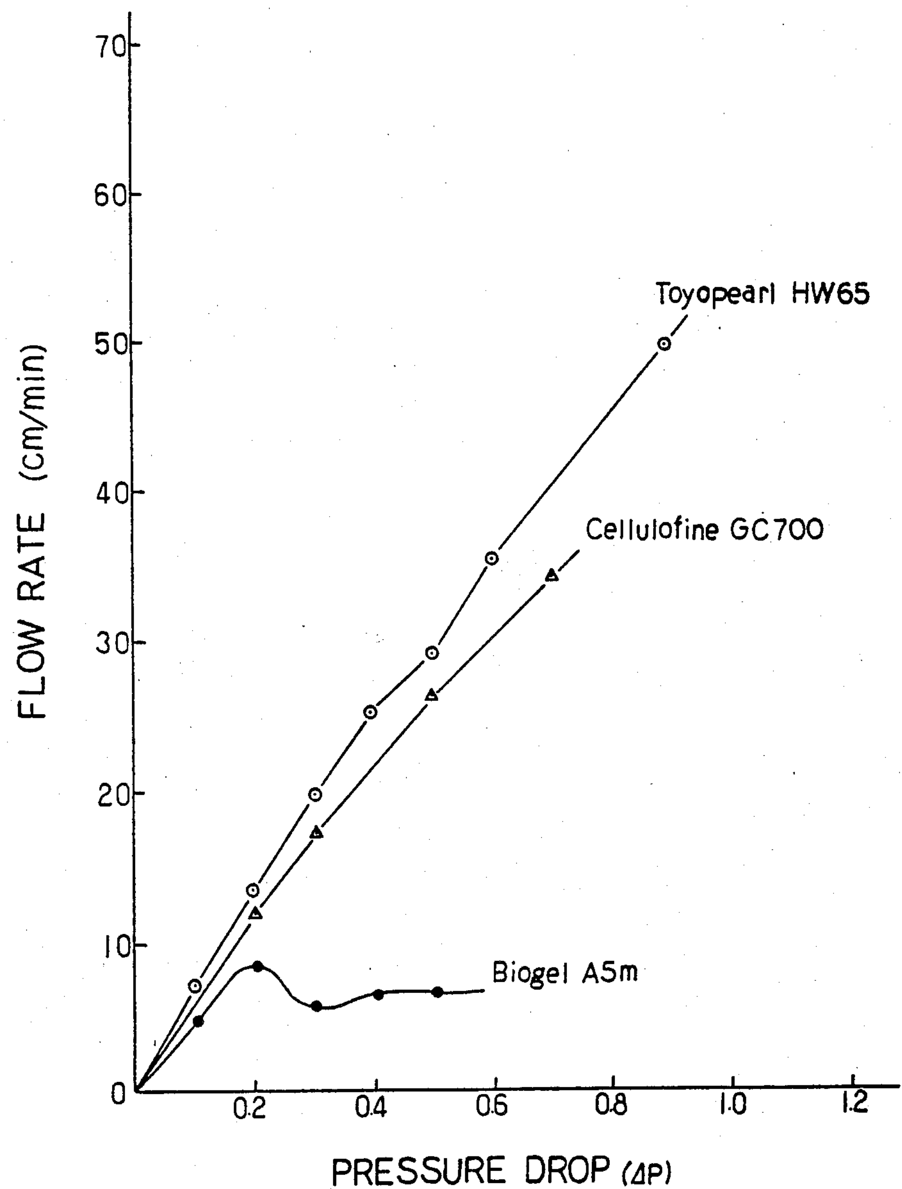
FIG. 1 is a graph showing a relation between a flow rate and a pressure drop obtained in Reference Example.

In the present invention, a water-insoluble porous hard gel of a polymer having hydroxy group in at least a part of the molecule is employed.

The above-mentioned water-insoluble porous hard gel of a polymer having hydroxy group in at least a part of the molecule may be a crystalline polymer, or it may be any polymer which is inherently water-insoluble by nature or made water-insoluble by cross-linking.

Non-limitative examples of the polymer having hydroxy group in at least a part of the molecule are, for instance, a polymer having an unit of the formula:

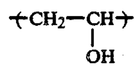

in at least a part of the molecule such as polyvinyl alcohol or hydrolysate of a copolymer of ethylene and vinyl acetate; a polymer having a unit of the formula:

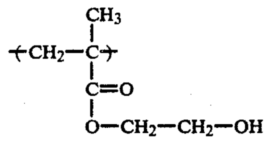

such as polyhydroxyethyl methacrylate, a copolymer containing hydroxyethyl methacrylate and the like; and polysaccharides such as cellulose, cellulose derivatives having hydroxy group including hydroxyethyl cellulose, agarose and dextran. In the above-mentioned examples, a polymer having a unit of the formula:

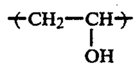

in at least a part of the molecule or polysaccharides is particularly preferable.

Hydroxy group in the polymer may be derived from a monomer capable of forming a polymer as in case of polyvinyl alcohol or polyhydroxyethyl methacrylate, or it may be introduced in the polymer by a chemical modification of the polymer, or it may be derived from the cross-linking agent which is used for forming an insoluble gel.

Non-limitative examples of the above-mentioned cross-linking agent, having hydroxy group or forming hydroxy group in the reaction, are typically polyvalent unsaturated compounds having hydroxy group such as pentaerythritol dimethacrylate, diallylidene pentaerythritol and glycerol dimethacrylate, or compounds having oxirane ring such as epichlorohydrin, butanediol diglycidyl ether and glycidyl methacrylate.

As previously mentioned, the cross-linking can be carried out during polymerization, after polymerization, or both during and after polymerization in order to obtain the water-insoluble polymer. The water-insoluble gel used in the present invention may be made water-insoluble by any type of the cross-linking such as cross-linking during polymerization, cross-linking after polymerization or cross-linking during and after polymerization as mentioned above. Further, the water-insoluble gel used in the present invention is required to be a hard gel.

The term "hard gel" herein referrs to a gel which is less swelled with a solvent and less deformed by a pressure than a soft gel such as dextran, agarose or acrylamide. A hard gel and a soft gel can be distinguished from each other in the following manner: i.e. as shown in the Reference Example herein below, when a relation between a flow rate and a pressure drop is determined by passing an aqueous liquid through a cylindrical column uniformly packed with a gel, a hard gel shows an almost linear relationship while a soft gel shows a non-linear relationship. In case of a soft gel, a gel is deformed and consolidated over a certain point of pressure and therefore a flow rate does not increase any more. In the present invention, a gel having the above linear relationship at least by 0.3 $kg/cm^2$ is referred to as "hard gel".

A hard gel is formed by various methods, any of which can be employed in the present invention.

In some case, only a soft gel is obtained when a water-insoluble gel is formed solely from a polymer having hydroxy group since, in general, such polymer exhibits a high degree of hydrophile property. In such case, however, a hard gel can be formed by employing the polymer having hydroxy group in combination with another polymer which but does not necessarily have hydroxy group but can form a hard gel.

In this case, formation of a hard gel can be carried out, for example, by mixing more than two kinds of polymer, or by coating a polymer having hydroxy group on the surface of a hard gel which is previously prepared. However, the present invention is not limited to these method.

The term "porous" in the present invention means that a gel has a porosity of not less than 20% and a specific surface of not less than 3 $m^2/g$.

A water-insoluble porous hard gel of a polymer having hydroxy group in at least a part of the molecule used in the present invention is required, in the first place, to have continuous pores with a large diameter so that LDL and VLDL, which are macromolecules having molecular weight of at least not less than $1\times10^6$, can easily enter in the pores to be adsorbed.

For measuring the pore size, there are various kinds of methods, among which mercury porosimetry is most frequently employed. In case of a hydrophilic gel, an exclusion limit is usually adopted as a measure of the pore size.

The term "exclusion limit" in the present invention means, as described in the literature such as "Jikken Kosoku Ekitai Chromatography (Experimental High Speed Liquid Chromatography)", Hiroyuki Hatano and Toshihiko Hanai, published by Kabushiki Kaisha Kagaku Dojin, the minimum molecular weight of the molecule which cannot permeate into a pore, i.e. which is excluded, in a gel permeation chromatography.

It is known that a value of an exclusion limit varies depending on a kind of the substances employed, among which an exclusion limit value with such molecules as globular proteins, dextran and polyethylene glycol has been quite investigated, whereas that with lipoproteins has been hardly investigated. Thus, in the present invention, a value of an exclusion limit measured by using globular proteins and/or viruses, which are regarded as the most similar substances to the lipoproteins, is suitably employed.

As the result of the investigation of the present inventors, using a variety of water-insoluble porous gels having a different value of an exclusion limit, it is unexpectedly shown that a gel having an exclusion limit value of about $1\times10^6$, which is smaller than the molecular weight of LDL and VLDL, can adsorb LDL and VLDL to some extent and that a gel having a larger pore size does not always exhibit an increased capacity of adsorbing but, conversely, it is observed that an adsorbing capacity of such gel decreases or proteins other than LDL and VLDL are likely to be adsorbed, which means there exist an optimum range of a pore size. That is, it is found that a water-insoluble porous hard gel having an exclusion limit of less than $1\times10^6$ can hardly adsorb LDL and VLDL and is not suited for practical use, whereas a water-insoluble porous hard gel having an exclusion limit of one million to several millions, which is nearly the molecular weight of LDL and VLDL, can adsorb LDL and VLDL to some extent. Subsequently, it is observed that an amount of an adsorbed LDL and VLDL increases with the increase of an exclusion limit, by and by reaching its top, and it extremely decreases when an exclusion limit is over $1\times10^8$ because in the region, a content of a polymer having hydroxy group in at least a part of the molecule, which makes up a water-insoluble porous hard gel, per volume of a gel is lowered and consequently an amount of hydroxy group per volume of gel is also lowered, thus a sufficient amount of sulfuric acid residue cannot be introduced in the polymer. Therefore, an exclusion limit of a water-insoluble porous hard gel employed in the present invention is $10^6$ to $10^8$, preferably $3\times10^6$ to $7\times10^7$.

With respect to a porous structure of a water-insoluble porous hard gel used in the present invention, a structure uniformly having pores at any part of the gel is more preferable than a structure having pores only on the surface of the gel for the purpose of adsorbing a larger amount of LDL and VLDL to be adsorbed.

A shape of a water-insoluble porous hard gel used in the present invention can be optionally selected from shapes such as particle, fiber, sheet and hollow fiber. When a water-insoluble porous hard gel with a shape of particle is used, the particle size is preferably 1 to 5000 μm.

There can be sulfated at least a part of hydroxy group in a water-insoluble porous hard gel by various methods such as, for instance, a method of reacting a water-insoluble porous hard gel having hydroxy group with chlorosulfonic acid or sulfuric anhydride in the presence of pyridine or N,N-dimethylformamide and a method of directly reacting hydroxy group with sulfuric acid in a solvent such as N,N-dimethylformamide. Though any method can be employed for sulfation of hydroxy group, sulfation is preferably carried out under anhydrous or nearly anhydrous conditions since such conditions can improve the efficiency of sulfation.

Since a water-insoluble porous hard gel of the present invention is converted to sulfate by the above-mentioned method, hydroxy group mainly on the surface of a water-insoluble porous hard gel is directly sulfated.

An amount of the introduced sulfuric acid residue is preferably 0.1 μmol to 10 mmol, more preferably 10 μmol to 1 mmol per 1 ml of a water-insoluble porous hard gel used in the present invention. When the amount is less than 0.1 μmol, a sufficient adsorbing capacity cannot be obtained. When the amount exceeds 10 mmol, nonspecific adsorption, especially an adsorption of fibrinogen increases and a pH change of the body fluids may be caused, which make the gel unsuitable for a practical usage.

The adsorbent according to the present invention can be used for treatment in various ways.

Most simply, the adsorbent of the present invention can be used as follows: i.e. blood is introduced outside the body of the patient to be put in a blood bag, with which the adsorbent of the present invention is mixed to adsorb LDL and VLDL, followed by removing the adsorbent through filter, the blood treated in this way being put back to the body of the patient. Though the method does not need an intricate apparatus, it has defects such that an amount of the blood treated at one time is small, it takes much time for treatment and an operation in the method is somewhat troublesome.

In another method, a column is packed with the adsorbent of the present invention, which is incorporated into an extracorporeal circulation circuit with circulation of the blood, wherein either whole blood is directly circulated or only plasma separated from the blood is passed through the column. Though the adsorbent of the present invention can be used in both of the above-mentioned methods, it is preferably used in the latter method as mentioned above.

Selectivity and efficiency of the removal of LDL and VLDL can be improved by adding, when using the adsorbent of the present invention, polyvalent metallic ion to blood or plasma to be treated. The examples of polyvalent metallic ion to be used for this purpose is, for instance, alkaline-earth metal ions such as calcium ion, magnesium ion, barium ion and strontium ion, ion of Group III of the Periodic Table such as aluminum ion, ion of Group VII of the Periodic Table such as manganese ion and ion of Group VIII of the Periodic Table such as cobalt ion.

By using the adsorbent of the present invention, LDL and VLDL can be selectively and effectively removed from the body fluids of the patient. Further, the adsorbent of the present invention can be prepared in a lower cost than the adsorbent based on the principle of the affinity chromatography, in which a relatively expensive ligand is employed.

The present invention is more specifically described and explained by the following Reference Example, Examples and Comparative Examples. It is to be understood that the present invention is not limited to the Reference Example, Examples and Comparative Examples and various changes and modifications can be made without departing from the scope and spirit of the present invention.

REFERENCE EXAMPLE

A relation between a flow rate and a pressure drop is determined by passing water by means of a peristaitic pump through cylindrical glass columns equipped at both ends with filters having a pore size of 15 μm (inner diameter: 9 mm, column length: 150 mm), in which an agarose gel (Biogel A5m made by Biorad Co., particle size: 50 to 100 mesh) and hard gels made of a polymer (Toyopearl HW 65 made by Toyo Soda Manufacturing Co., Ltd., particle size: 50 to 100 μm, and Cellulofine GC-700 made by Chisso Corporation, particle size: 45 to 105 μm) are filled respectively. The results were shown in FIG. 1.

As shown in FIG. 1, an increase of a flow rate is nearly proportional to that of a pressure in case of hard gels made of a polymer, whereas in case of an agarose gel, consolidation occurrs and a flow rate does not increase even if a pressure increases.

EXAMPLE 1

There was dried 10 ml of cross-linked polyacrylate gel (Toyopearl HW 75, exclusion limit of proteins: $5\times10^6$, particle size: 50 to 100 μm), which was a hard gel having pores at any part thereof, by a critical point drying method in ethanol. The resultant dried gel was suspended in 10 ml of N,N-dimethylformamide sufficiently dehydrated and the suspension was cooled with ice, to which 1 ml of chlorosulfonic acid was added dropwise under stirring, the stirring being continued for 10 minutes after the dropwise addition was completed. After completion of the reaction, the reaction mixture was neutralized with 10% aqueous solution of sodium hydroxide, the gel being filtered and washed with a great excess of water to give a water-insoluble porous hard gel on whose surface 0.4 mmol/ml of sulfuric acid residue was introduced.

EXAMPLE 2

A method described in Example of Japanese Unexamined Patent Publication No. 12656/1983 was employed, i.e. a uniform mixture of 100 g of vinyl acetate, 24.1 g of triallyl isocyanurate, 124 g of ethyl acetate, 124 g of heptane, 3.1 g of polyvinyl acetate (degree of polymerization: 500) and 3.1 g of 2,2'-azobisisobutyronitrile, and 400 ml of water in which 1% by weight of polyvinyl alcohol, 0.05% by weight of sodium dihydrogenphosphate.$2H_2O$ and 1.5% by weight of disodium hydrogenphosphate.$12H_2O$ were dissolved were charged in flask. After sufficient stirring, a suspension polymerization was carried out by stirring the mixture for 18 hours at 56.5° C., further for 5 hours at 75° C. to give a granular copolymer, which was then filtered, washed with water, extracted with acetone and subjected to an ester interchange reaction for 18 hours at 40° C. in a solvent of 46.5 g of sodium hydroxide and 2 l of methanol. There was dried 10 ml of the thus obtained water-insoluble porous hard gel having vinyl alcohol as a main constitutional unit (exclusion limit: about $1.8\times10^6$, average particle size: 150 μm) by a critical point drying method in acetone. The resultant dried gel was suspended in 10 ml of N,N-dimethylformamide sufficiently dehydrated and the suspension was cooled with ice, to which 1 ml of chlorosulfonic acid was added dropwise under stirring, the stirring being continued for 10 minutes after the dropwise addition was completed. After completion of the reaction, the reaction mixture was neutralized with 10% aqueous solution of sodium hydroxide, the gel being filtered and washed sufficiently with water to give a water-insoluble porous hard gel on whose surface 0.8 mmol/ml of sulfuric acid residue was introduced.

EXAMPLES 3 TO 4 AND COMPARATIVE EXAMPLE 1

There was added 6 ml of plasma obtained from the patient suffering from a familial hyperlipemia to 1 ml of each gel in a test tube prepared in Examples 1 and 2 respectively and the resultant mixture was incubated under stirring for 2 hours at 37° C. (Examples 3 and 4). An amount of LDL, VLDL, HDL cholesterol and fibrinogen in each supernatant was determined. The results were shown in Table 1.

An amount of LDL, VLDL, HDL cholesterol and fibrinogen in case that the adsorbent was not added was also determined. The result was shown in Table 1 (Comparative Example 1).

TABLE 1

| | Adsorbent | | | | | |
|---|---|---|---|---|---|---|
| Example No. | Type of adsorbent | An amount of sulfuric acid residue (mmol/ml) | LDL (mg/dl) | VLDL (mg/dl) | HDL cholesterol Fibrinogen (mg/dl) | |
| 3 | Adsorbent prepared in Example 1 | 0.4 | 282 | 28 | 19 | 216 |
| 4 | Adsorbent prepared in Example 2 | 0.8 | 546 | 71 | 19 | 203 |
| Comparative Example 1 | None | 0 | 830 | 92 | 20 | 228 |

As shown in Table 1, both LDL and VLDL were adsorbed whereas HDL cholesterol and fibrinogen were hardly adsorbed by using the adsorbent according to the present invention.

EXAMPLE 5

There was dried 10 ml of a porous cellulose gel (CK gel A-3 made by Chisso Corporation, exclusion limit of globular proteins: $5\times10^7$, particle size: 45 to 105 μm) by a critical point drying method in ethanol. The resultant dried gel was suspended in 10 ml of pyridine sufficiently dehydrated and the suspension was cooled with ice, to which 2 ml of chlorosulfonic acid was added dropwise under stirring, the stirring being continued for 10 minutes after the dropwise addition was completed. After completion of the reaction, the gel was filtered and washed successively with pyridine and water to give a cellulose gel on whose surface was introduced sulfuric acid residue in an amount shown in Table 2.

EXAMPLE 6

There was dried 10 ml of a porous cellulose gel (Cellulofine GCL-2000 made by Chisso Corporation, exclusion limit of globular proteins: $3\times10^7$, particle size: 45 to 105 μm, a cross-linked gel) by a critical point drying method in ethanol. The resultant dried gel was suspended in 10 ml of pyridine sufficiently dehydrated and the suspension was cooled with ice, to which 2 ml of chlorosulfonic acid was added dropwise under stirring, the stirring being continued for 10 minutes after the dropwise addition was completed. After completion of the reaction, the gel was filtered and washed successively with pyridine and water to give a cellulose gel on whose surface was introduced sulfuric acid residue in an amount shown in Table 2.

EXAMPLE 7

There was dried 10 ml of CK gel A-3 by a critical point drying method in ethanol. The resultant dried gel was suspended in 10 ml of dimethylformamide sufficiently dehydrated, to which 12 ml of a solution of 4M N,N-dicyclohexylcarbodiimide/dimethylformamide was added and the resultant was cooled with ice, to which 6 ml of a solution of 2M sulfuric acid/dimethylformamide was added dropwise under stirring, the stirring being continued for 2 hours at 0° C. After completion of the reaction, the gel was filtered and washed successively with dimethylformamide and water to give a cellulose gel on whose surface was introduced sulfuric acid residue in an amount shown in Table 2.

EXAMPLE 8

There was dried 10 ml of Cellulofine GCL-2000 by a critical point drying method in ethanol. The resultant dried gel was suspended in 10 ml of dimethylformamide sufficiently dehydrated, to which 12 ml of a solution of 4M N,N-dicyclohexylcarbodiimide/dimethylformamide was added and the resultant was cooled with ice, to which 6 ml of a solution of 2M sulfuric acid/dimethylformamide was added dropwise under stirring, the stirring being continued for 2 hours at 0° C. After completion of the reaction, the gel was filtered and washed successively with dimethylformamide and water to give a cellulose gel on whose surface was introduced sulfuric acid residue in an amount shown in Table 2.

EXAMPLES 9 TO 10

The procedures of Example 5 were repeated except that 6 ml of chlorosulfonic acid and 8 ml of chlorosulfonic acid were used (Example 9 and Example 10 respectively) to give a cellulose gel on whose surface was introduced sulfuric acid in an amount shown in Table 2.

COMPARATIVE EXAMPLE 2

The procedures of Example 5 were repeated except that Cellulofine GC 700 (made by Chisso Corporation, exclusion limit of globular proteins: $4\times10^5$, particle size: 45 to 105 $\mu$m) was used as a cellulose gel to give a cellulose gel on whose surface was introduced sulfuric acid in an amount shown in Table 2 .

EXAMPLES 11 TO 16 AND COMPARATIVE EXAMPLES 3 TO 4

Each 1 ml of gel prepared in Examples 5 to 10 and Comparative Example 2 respectively were put in a test tube, to which 6 ml of plasma obtained from the patient suffering from a familial hyperlipemia was added and the resultant was incubated for 2 hours at 37° C. under stirring (Examples 11 to 16 and Comparative Example 3 respectively).

An amount of LDL, VLDL, HDL cholesterol and fibrinogen was determined The results were shown in Table 2.

An amount of LDL, VLDL, HDL cholesterol and fibrinogen in case that the gel was not added was also determined (Comparative Example 3). The result was shown in Table 2.

TABLE 2

| | Adsorbent | | | | | |
|---|---|---|---|---|---|---|
| Example No. | Type of adsorbent | An amount of sulfuric acid residue (mmol/ml) | LDL (mg/dl) | VLDL (mg/dl) | HDL cholesterol (mg/dl) | Fibrinogen |
| 11 | Adsorbent prepared in Example 5 | 0.05 | 386 | 25 | 20 | 220 |
| 12 | Adsorbent prepared in Example 6 | 0.08 | 535 | 66 | 21 | 226 |
| 13 | Adsorbent prepared in Example 7 | 0.16 | 274 | 25 | 20 | 218 |
| 14 | Adsorbent prepared in Example 8 | 0.20 | 512 | 68 | 20 | 221 |
| 15 | Adsorbent prepared in Example 9 | 0.6 | 246 | 30 | 19 | 204 |
| 16 | Adsorbent prepared in Example 10 | 1.2 | 365 | 47 | 20 | 185 |
| Comparative Example 3 | Adsorbent prepared in Comparative Example 2 | 0.5 | 765 | 89 | 20 | 220 |
| Comparative Example 4 | None | 0 | 840 | 95 | 21 | 230 |

What we claim is:

1. A lipoprotein adsorbent for use in extracorporeal circulation treatment which is made of a water-insoluble porous hard gel which has an exclusion limit value from $10^6$ to $10^9$ measured by using glubular proteins and comprises a polymer having hydroxy group in at least a part of the molecule, at least a part of hydroxy groups on the surface of said gel being converted to sulfates.

2. The lipoprotein adsorbent of claim 1, wherein said polymer having hydroxy group in at least a part of the molecule is a polymer having a unit of the formula:

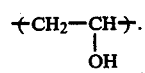

3. The lipoprotein adsorbent of claim 1, wherein said polymer having hydroxy group in at least a part of the molecule is a polysaccharide.

4. The lipoprotein adsorbent of claim 3, wherein said polysaccharide is a cellulose.

* * * * *